(12) United States Patent
Sahai et al.

(10) Patent No.: US 9,486,555 B2
(45) Date of Patent: Nov. 8, 2016

(54) POLYHEDRAL OLIGOMERIC SILSESQUIOXANE (POSS)-BASED BIOACTIVE HYBRID GLASS AS A SCAFFOLD FOR HARD TISSUE ENGINEERING

(71) Applicants: Nita Sahai, Akron, OH (US); Xianfeng Zhou, Akron, OH (US)

(72) Inventors: Nita Sahai, Akron, OH (US); Xianfeng Zhou, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/689,808

(22) Filed: Apr. 17, 2015

(65) Prior Publication Data

US 2015/0297788 A1 Oct. 22, 2015

Related U.S. Application Data

(60) Provisional application No. 61/980,923, filed on Apr. 17, 2014.

(51) Int. Cl.
*A61L 27/18* (2006.01)
*C08G 77/04* (2006.01)
*A61L 27/54* (2006.01)

(52) U.S. Cl.
CPC ............... *A61L 27/18* (2013.01); *A61L 27/54* (2013.01); *C08G 77/045* (2013.01); *A61L 2300/102* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 6,100,417 A | * | 8/2000 | Lichtenhan | C07F 7/21 528/25 |
| 2006/0083925 A1 | * | 4/2006 | Laine | C07F 7/21 428/405 |
| 2006/0188732 A1 | * | 8/2006 | Lichtenhan | B82Y 30/00 428/447 |
| 2009/0012317 A1 | * | 1/2009 | Laine | C07F 7/21 549/215 |
| 2012/0277372 A1 | * | 11/2012 | Hu | C08G 77/04 524/588 |

* cited by examiner

*Primary Examiner* — Robert S Loewe
(74) *Attorney, Agent, or Firm* — Renner Kenner Greive Bobak Taylor & Weber

(57) ABSTRACT

A hybrid bioactive glass comprising a plurality of POSS-cages each having at least one flexible arm radiating from an Si atom of the POSS-cage, each POSS-cage being covalently linked to another POSS-cage through an Si—O—Si linkage between two flexible arms. A method of forming a hybrid bioactive glass comprising the steps of providing a plurality of POSS-cages, each having at least one reactive flexible arm radiating from an Si atom detailed by —X—Si[$R_1,R_2,R_3$], wherein X is an arm extension located between the Si—O—Si linkage and an Si atom of the POSS-cage, wherein $R_1$, $R_2$ and $R_3$ are also the same or different, and at least one of the $R_1$, $R_2$ and $R_3$ is an alkoxide, and reacting the plurality of POSS-cages through a sol-gel method to form a covalently-linked network and incorporating $Ca^{+2}$ ions therein, the sol-gel process comprising hydrolysis and polycondensation reactions of the plurality of POSS-cages.

19 Claims, 6 Drawing Sheets

Fig. 10

POLYHEDRAL OLIGOMERIC SILSESQUIOXANE (POSS)-BASED BIOACTIVE HYBRID GLASS AS A SCAFFOLD FOR HARD TISSUE ENGINEERING

CROSS-REFERENCE TO RELATED APPLICATIONS

The present application claims priority to U.S. Provisional Patent Application Ser. No. 61/980,923, filed Apr. 17, 2014, the entirety of which is incorporated herein by reference.

STATEMENT REGARDING FEDERALLY SPONSORED RESEARCH OR DEVELOPMENT

This invention was made with government support under 0906817 awarded by the National Science Foundation, Materials Research (NSF DMR). The government has certain rights in the invention.

FIELD OF THE INVENTION

The present invention generally relates to a hybrid bioactive glass. The hybrid bioactive glass is based on a polyhedral oligomeric silsesquioxane (POSS) network, with POSS cages covalently link to one another to form a network-like structure through Si—O—Si linkages. In some embodiments, calcium ion ($Ca^{+2}$) is retained by the bioactive glass, and released thereby to promote hydroxyapatite (HAp) formation and bioactivity.

BACKGROUND OF THE INVENTION

In conventional tissue engineering applications, a key tenet is to develop scaffold materials that can match native tissue mechanical properties and stimulate stem cell differentiation for tissue regeneration.

Living bone is a composite of hard mineral nanoparticles (hydroxyapatite, HAp) and organic fibrous collagen with intricate nanoarchitectures that make up this tough, hard tissue. Past attempts have been made to simulate these nanostructures in synthetic materials. Despite some advances in the field, it is synthetically difficult to achieve the complex nanostructures. In materials science, the manner in which to mimic biological systems to design and fabricate bio-inspired bulk materials remains a grand challenge.

The complex nanostructures of nature are considered essential for the design of tough biomimetic materials. However, biomimetic materials of the future do not necessarily mimic the exact tissue or organ-like complex nanostructures. Instead, by understanding and incorporating the extremely efficient mechanisms of fracture resistance developed by nature, the materials will be bio-inspired in function but not necessarily in shape.

Therefore, there is a need in the art for robust bio-inspired materials for the construction of hybrid materials with well-defined nanostructures that can covalently bond to inorganic nanoparticles on a molecular scale, allowing the inorganic particles to deform elastically on a limited scale, which allow for better mechanical properties, especially fracture toughness. These nanostructures allow the bulk materials to possess the mechanical properties of natural hybrids while simultaneously maintaining the desired bioactivity of purely inorganic materials, resulting in the benefit of better mechanical properties with increased bioactivity.

The present invention utilizes well-defined nanostructures formed through the sol-gel process using well-designed single-component molecular precursor. The new silica-based scaffold materials support stem cell growth and differentiation for bone tissue engineering. The present invention provides a hybrid bioactive glass with increased mechanical properties, such as increased toughness, while maintaining bioactivity, especially for bone and teeth applications.

SUMMARY OF THE INVENTION

In a first embodiment, the present invention provides a hybrid bioactive glass. The hybrid bioactive glass comprising a plurality of POSS-cages each having at least one flexible arm radiating from an Si atom of the POSS-cage, each POSS-cage being covalently linked to another POSS-cage through an Si—O—Si linkage between two of said flexible arms.

In a second embodiment, the present invention provides a hybrid bioactive glass as in the first embodiment, wherein each POSS-cage is covalently bonded to at least 2 other POSS-cages.

In a third embodiment, the present invention provides a hybrid bioactive glass as in either the first or second embodiment, wherein each POSS-cage is covalently bonded to at least 3 other POSS-cages.

In a fourth embodiment, the present invention provides a hybrid bioactive glass as in any of the first through third embodiments, wherein each POSS-cage is covalently bonded to at least 4 other POSS-cages.

In a fifth embodiment, the present invention provides a hybrid bioactive glass as in any of the first through fourth embodiments, wherein each POSS-cage is covalently bonded to at least 5 other POSS-cages.

In a sixth embodiment, the present invention provides a hybrid bioactive glass as in any of the first through fifth embodiments, wherein each POSS-cage is covalently bonded to at least 6 other POSS-cages.

In a seventh embodiment, the present invention provides a hybrid bioactive glass as in any of the first through sixth embodiments, wherein each POSS-cage is covalently bonded to at least 7 other POSS-cages.

In an eighth embodiment, the present invention provides a hybrid bioactive glass as in any of the first through seventh embodiments, wherein each POSS-cage is covalently bonded to at least 8 other POSS-cages.

In a ninth embodiment, the present invention provides a hybrid bioactive glass as in any of the first through eighth embodiments, wherein the flexible arms include an arm extension between the Si—O—Si linkage and the Si atom of the POSS cage, the arm extension being an alkane chain of 10 carbon atoms or less.

In a tenth embodiment, the present invention provides a hybrid bioactive glass as in any of the first through ninth embodiments, wherein the flexible arms include an arm extension between the Si—O—Si linkage and the Si atom of the POSS cage, the arm extension being an alkane chain of 9 carbon atoms or less.

In an eleventh embodiment, the present invention provides a hybrid bioactive glass as in any of the first through tenth embodiments, wherein the flexible arms include an arm extension between the Si—O—Si linkage and the Si atom of the POSS cage, the arm extension being an alkane chain of 8 carbon atoms or less.

In a twelfth embodiment, the present invention provides a hybrid bioactive glass as in any of the first through eleventh embodiments, wherein the flexible arms include an arm extension between the Si—O—Si linkage and the Si atom of the POSS cage, the arm extension being an alkane chain of 7 carbon atoms or less.

In a thirteenth embodiment, the present invention provides a hybrid bioactive glass as in any of the first through twelfth embodiments, wherein the flexible arms include an arm extension between the Si—O—Si linkage and the Si atom of the POSS cage, the arm extension being an alkane chain of 6 carbon atoms or less.

In a fourteenth embodiment, the present invention provides a hybrid bioactive glass as in any of the first through thirteenth embodiments, wherein the flexible arms include an arm extension between the Si—O—Si linkage and the Si atom of the POSS cage, the arm extension being an alkane chain of 5 carbon atoms or less.

In a fifteenth embodiment, the present invention provides a hybrid bioactive glass as in any of the first through fourteenth embodiments, wherein the flexible arms include an arm extension between the Si—O—Si linkage and the Si atom of the POSS cage, the arm extension being an alkane chain of 4 carbon atoms or less.

In a sixteenth embodiment, the present invention provides a hybrid bioactive glass as in any of the first through fifteenth embodiments, wherein the flexible arms include an arm extension between the Si—O—Si linkage and the Si atom of the POSS cage, the arm extension being an alkane chain of 3 carbon atoms or less.

In a seventeenth embodiment, the present invention provides a hybrid bioactive glass as in any of the first through sixteenth embodiments, wherein the flexible arms include an arm extension between the Si—O—Si linkage and the Si atom of the POSS cage, the arm extension being an alkane chain of at least 2 carbon atoms.

In an eighteenth embodiment, the present invention provides a hybrid bioactive glass as in any of the first through seventeenth embodiments, wherein the POSS-cage comprises a cage structure selected from one of (i) 6 Si atoms, (ii) 8 Si atoms, (iii) 10 Si atoms, or (iv) 12 Si atoms.

In a nineteenth embodiment, the present invention provides a hybrid bioactive glass as in any of the first through eighteenth embodiments, wherein the POSS-cage comprises a cage structure of 8 Si atoms.

In a twentieth embodiment, the present invention provides a method of forming a hybrid bioactive glass as in any of the first through nineteenth embodiments, wherein the method of forming a hybrid bioactive glass comprising the steps of providing a plurality of POSS-cages, each having at least one reactive flexible arm radiating from an Si atom, wherein the reactive flexible arm is detailed by —X—Si[$R_1,R_2,R_3$], wherein X is an arm extension located between the Si—O—Si linkage and an Si atom of the POSS-cage, wherein $R_1$, $R_2$ and $R_3$ are also the same or different, and at least one of said $R_1$, $R_2$ and $R_3$ is an alkoxide, and reacting the plurality of POSS-cages through a sol-gel method employing a calcium alkoxide to form a covalently-linked network and incorporate $Ca^{+2}$ ions into the covalently-linked network so formed, the sol-gel process comprising hydrolysis and polycondensation reactions.

In a twenty-first embodiment, the present invention provides a method of forming a hybrid bioactive glass as in any of the first through twentieth embodiments, wherein at least one of the $R_1$, $R_2$ and $R_3$ is selected from —$OC_nH_{2n+1}$.

In a twenty-second embodiment, the present invention provides a method of forming a hybrid bioactive glass as in any of the first through twenty-first embodiments, wherein n is less than 10.

In a twenty-third embodiment, the present invention provides a method of forming a hybrid bioactive glass as in any of the first through twenty-second embodiments, wherein $R_1$ is an ethoxy group.

In a twenty-fourth embodiment, the present invention provides a method of forming a hybrid bioactive glass as in any of the first through twenty-third embodiments, wherein $R_1$ is a methoxy group.

In a twenty-fifth embodiment, the present invention provides a method of forming a hybrid bioactive glass as in any of the first through twenty-fourth embodiments, wherein $R_1$ is a propoxy group.

In a twenty-sixth embodiment, the present invention provides a method of forming a hybrid bioactive glass as in any of the first through twenty-fifth embodiments, wherein the hydrolysis reaction of the step of reacting employs a solvent and an acid catalyst.

In a twenty-seventh embodiment, the present invention provides a method of forming a hybrid bioactive glass as in any of the first through twenty-sixth embodiments, wherein the solvent is ethanol.

In a twenty-eighth embodiment, the present invention provides a method of forming a hybrid bioactive glass as in any of the first through twenty-seventh embodiments, wherein the acid catalyst is HCl.

In a twenty-ninth embodiment, the present invention provides a method of forming a hybrid bioactive glass as in any of the first through twenty-eighth embodiments, wherein the sol-gel method incorporates calcium alkoxide during the polycondensation reaction.

BRIEF DESCRIPTION OF THE DRAWINGS

FIG. 10 is a table showing a comparison of the FTIR absorption bands in the hybrid bioactive glass and the SGA.

DETAILED DESCRIPTION OF ILLUSTRATIVE EMBODIMENTS

Figure 1:
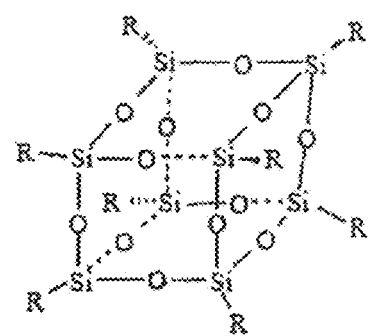
FIG. 1 shows the chemical formula of an exemplary polyhedral oligomeric silsesquioxane (POSS) employed in the present invention.
Figure 2:
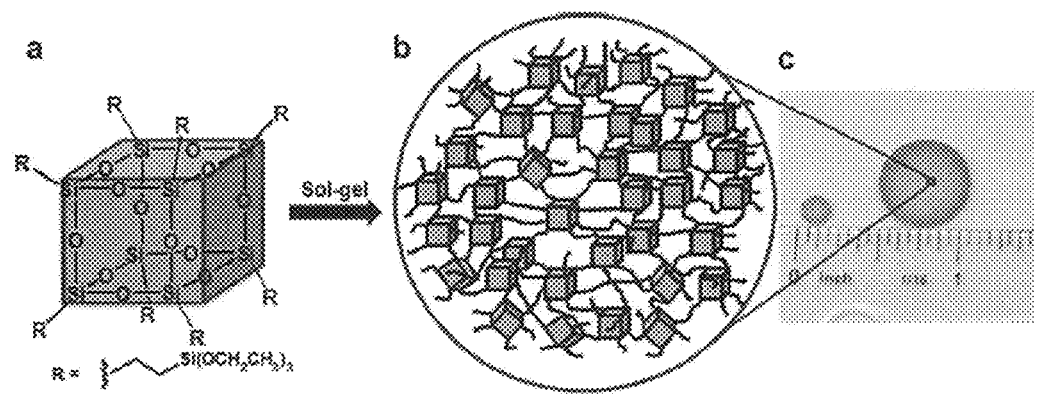
FIG. 2 is a general schematic of the process of the present invention, showing a starting POSS reagent (at a), a schematic representation of the network formed by a sol-gel method (at b), and an image of the end product hybrid glass (at c).

The present invention provides a POSS-based hybrid bioactive glass with superior mechanical properties and in vitro bioactivity. The POSS-based hybrid bioglass can be used to develop scaffold materials that can match native tissue mechanical properties and stimulate stem cell differentiation for tissue regeneration. The POSS-based hybrid bioglass of the present invention exhibits ideal characteristics for calcium phosphate nucleation and accurately mimics in vivo bone mineral maturation, which are necessary requirements for successful bone tissue engineering. The POSS-based hybrid bioglass has particular applications in dental implants or other areas where bone growth is needed, since living bone is a composite of hard mineral nanoparticles, called hydroxyapatite.

This POSS-based hybrid bioglass is formed to provide better properties than the well-known "star-gel" materials (developed by DuPont Corporation™, Wilmington, Del., USA) and could be more successful than conventional dendrimer cores due to their rigid silsesquioxane structure, which would facilitate the construction of uniform gel network architecture with better mechanical properties.

In some embodiments, the POSS-based hybrid bioglass is formed by covalently bonding a plurality of POSS-cages, each having at least one reactive flexible arm radiating from an Si atom of the POSS-cage. In some embodiments, each POSS-cage is covalently linked to another POSS-cage through an Si—O—Si linkage between two of reactive flexible arms. When covalently linked (i.e. when the hybrid bioglass is formed) these "reactive flexible arms" can be referred to as "flexible arms" since they have already reacted.

In some embodiments, the POSS-based hybrid bioglass includes a plurality of POSS-cages, each having at least one flexible arm radiating from an Si atom of the POSS-cage.

In some embodiments, the pluralities of POSS-cages have at least two flexible arms radiating from their own unique Si-atom of the POSS-cage. In other embodiments, the pluralities of POSS-cages have at least three flexible arms radiating from their own unique Si atom of the POSS-cage, in other embodiments, at least four flexible arms, in other embodiments, at least five flexible arms, and in other embodiments, at least six flexible arms. In such embodiments, the six flexible arms would account for every Si atom of the six Si atom POSS-cage. In other embodiments, the pluralities of POSS-cages have at least seven flexible arms radiating from their own unique Si atom of the POSS-cage. In other embodiments, the pluralities of POSS-cages have at least eight flexible arms radiating from their own unique Si atom of the POSS-cage. In such embodiments, the eight flexible arms would account for every Si atom of the eight Si atom POSS-cage.

It should be appreciated that it is not required that all flexible arms participate in an Si—O—Si linkage. In some embodiments, where each POSS-cage includes at least one flexible arm, at least one flexible arm but less than all flexible arms which radiate from each Si atom, will participate in an Si—O—Si linkage. In some embodiments, multiple flexible arms might remain unlinked.

In some embodiments, the hybrid glass of the present invention is made bioactive by the incorporation of $Ca^{+2}$ ions into the composite matrix. Without wanted to be bound by a particular theory, it is believed the $Ca^{+2}$ may be in close proximity and could be attracted to the negative charge of the deprotonated sianol group, Si—OH, during the sol-gel method.

In the process for creating the bioglass of the present invention, polyhedral oligomeric silsesquioxanes, also known as POSS, are employed. POSSs are a family of molecules with different numbers of silicon and oxygen atoms and are unique in that they are physically large (approx. 1.5 nm in diameter and 1000 amu) and are composed of robust silicon-oxygen framework that can be easily functionalized with a variety of organic substituents.

The hybrid bioglass of the present invention is a network of a plurality of POSS-cages. In some embodiments, each POSS-cage has a cage structure of 6 or 8 or 10 or 12 Si atoms. Such structures are particularly attractive as core materials because of the minimal number of required syntheses steps and their polyhedral structures can produce spherically symmetric network-like molecules.

In some embodiments, the POSS-cage has the general formula $R_nSi_nO_{1.5n}$. In some embodiments, the plurality of POSS-cages take one or more of the following forms:

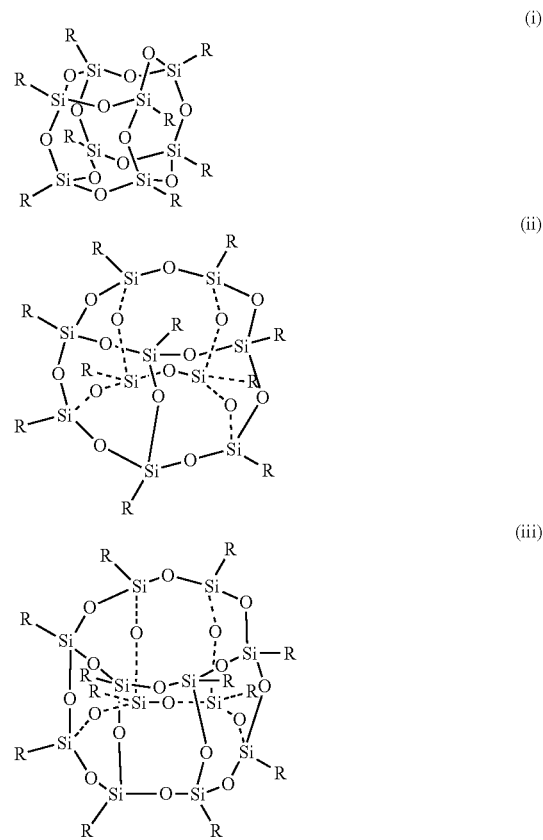

wherein the R represents organic groups, and at least one R group is a flexible arm suitable for joining the POSS-cage to a flexible arm of another POSS cage through an Si—O—Si linkage.

In some embodiments, each POSS-cage includes at least one reactive flexible arm radiating from an Si atom of the POSS-cage. It can be appreciated that with a higher number of reactive flexible arms that each POSS-cage includes, there will be an increase in networking and therefore an increase in the mechanical properties of the hybrid bioactive glass. Such mechanical properties include an increase in strength and fracture toughness.

In some embodiments, the hybrid bioactive glass exhibits enhanced structural effects, such as increased stiffness or strength of the material. Measured by Young's modulus, the measure of stiffness mainly depends on elastic forces of the chemical bonds of the hybrid network, in which a higher modulus is representative of a higher stiffness or strength. Upon information and belief, the high modulus can be achieved due to the higher Si—O inorganic composition and higher Peirels-Nabarro forces that limit dislocation mobility associated within the rigid POSS-cage structure.

In some embodiments, the hybrid bioactive glass exhibits a Young's modulus of 500-1000 MPa. In other embodiments, the hybrid bioactive glass exhibits a Young's modulus of 500-900 MPa, in other embodiments, 600-800 MPa, in other embodiments, 600-800 MPa, in other embodiments, 700-800 MPa, and in other embodiments, 750-800 MPa.

In some embodiments, the hybrid bioactive glass exhibits enhanced structural effects, such as increased fracture toughness, due to the structure of the POSS-cages. In some embodiments, the increased fracture toughness is analogous to the fracture toughness of a human tibia. The structure of the POSS-cages allows the hybrid bioactive glass to replicates the nanoscale phenomena observed in natural materials, like those found in bone and dental enamel. In some embodiments, the bonds located on each POSS-cage can act as elastic springs, as well as sacrificial bonds, which make the POSS cage undergo "elastic deformation" to dissipate energy. In some embodiments, the POSS-cage network includes some unoccupied spaces between molecules due to the steric effects associated with the POSS structure. Upon information and belief, the unoccupied spaces contribute to the high intermolecular force and contribute to the high fracture toughness of the hybrid bioactive glass.

In some embodiments, the hybrid bioactive glass exhibits a fracture toughness of between 0.5-10 MPa·m$^{1/2}$. In other embodiments, the hybrid bioactive glass exhibits a fracture toughness of between 1.5-8 MPa·m$^{1/2}$, in other embodiments, between 2.5-6.5 MPa·m$^{1/2}$, in other embodiments, between 3.5-6 MPa·m$^{1/2}$, and in some embodiments, between 2.4-5.3 MPa·m$^{1/2}$. In some embodiments, the hybrid bioactive glass exhibits a fracture toughness of 3.56 MPa·m$^{1/2}$.

As shown in FIG. 1, for example, a POSS-cage having 8 silicon atoms includes eight reactive flexible arms. In some embodiments, each POSS-cage includes at least two reactive flexible arms. In other embodiments, each POSS-cage includes at least three reactive flexible arms, in other embodiments, at least four flexible arms, in other embodiments, at least five reactive flexible arms, and in other embodiments, at least six reactive flexible arms. In some embodiments, each POSS-cage includes at least one reactive flexible arm radiating from each Si atom included in the POSS-cage.

It should be appreciated that each flexible arm provides the functionality to covalently link to another flexible arm of another POSS-cage through an Si—O—Si bond. The covalent linkages are formed through covalent Si—O—Si bonds between a flexible arm from one POSS-cage and a flexible arm from another POSS-cage.

In some embodiments, each POSS-cage is covalently bonded to at least 2 other POSS-cages. In other embodiments, each POSS-cage is covalently bonded at least 3 other POSS-cages, in other embodiments, at least 4 other POSS-cages, in other embodiments, at least 5 other POSS-cages, in other embodiments, at least 6 other POSS-cages, in other embodiments, at least 6 other POSS-cages, and in other embodiments, at least 8 other POSS-cages. It should be appreciated that the mechanical properties of the hybrid bioactive glass will change according to the network.

As shown in FIG. 1, in some embodiments the flexible arms of the present invention are represented by R. Each flexible arm, R, extends from an Si atom of the POSS-cage and provides the ability for a POSS-cage to covalently link to another POSS-cage by forming an Si—O—Si linkage. In some embodiments, the flexible arm R is characterized by the formula —X—Si[R$_1$,R$_2$,R$_3$], wherein R$_1$, R$_2$ and R$_3$ are the same or different, and at least one of said R$_1$, R$_2$ and R$_3$ is an alkoxide. The ability of the plurality of POSS-cages to form a covalently-linked network is provided by the alkoxide, which serves to form the Si—O—Si bond through a sol-gel method.

In some embodiments, at least R$_1$ is selected from an alkoxide group, characterized as —OC$_n$H$_{2n+1}$. In some embodiments, at least R$_1$ is selected from an alkoxide group, characterized as —OC$_n$H$_{2n+1}$, wherein n is less than 10. In some embodiments, at least R$_1$ is an alkoxide is selected from methoxide, ethoxide, propoxide, or the like.

In some embodiments, R$_1$, R$_2$ and R$_3$ are all alkoxides, characterized as —OC$_n$H$_{2n+1}$. In some embodiments, R$_1$, R$_2$ and R$_3$ are all alkoxides, characterized as —OC$_n$H$_{2n+1}$, wherein n is less than 10. In some embodiments, R$_1$, R$_2$ and R$_3$ are all alkoxides, wherein each alkoxide is selected from methoxide, ethoxide, propoxide, or the like.

In some embodiments, such as that represented in the general formula above, each flexible arm R includes an arm extension, X. In the resultant hybrid bioglass, the arm extension, X, is located between the Si—O—Si linkage and an Si atom of the POSS-cage. In some embodiments, the arm extension is an alkane chain.

It should be appreciate that with an increase in the number of carbons within the alkane chain, there will be a decrease in strength of the hybrid bioactive glass, the arms providing flexibility between POSS cages in the network structure. In some embodiments, the alkane chain includes 10 carbons or less, in other embodiments, 9 carbons or less, in other embodiments, 8 carbons or less, in other embodiments, 7 carbons or less, in other embodiments, 6 carbons or less, in other embodiments, 5 carbons or less, in other embodiments, 4 carbons or less, in other embodiments, 3 carbons or less, and in other embodiments 2 carbons.

In some embodiments, the arm extension can include any of the following type of bonds: carbon-nitrogen (C—N) bonds, a carbon-carbon (C—C), carbon-sulfur (C—S), and carbon-oxygen (C—O) bonds. In some embodiments, the extension includes 10 such bonds or less, in other embodiments, 9 bonds or less, in other embodiments, 8 bonds or less, in other embodiments, 7 bonds or less, in other embodiments, 6 bonds or less, in other embodiments, 5 bonds or less, in other embodiments, 4 bonds or less, in other embodiments, 3 bonds or less, and in other embodiments 2 bonds. That is, in various embodiments, the linkage is from 2 to 10 atoms in length, chosen from the various bonds provided in this paragraph.

In some embodiments, the hybrid bioactive glass of the present invention is formed by reacting a plurality of POSS-cages to form a covalently-linked network by creating Si—O—Si linkages from a "sol-gel" method.

The present invention utilizes the sol-gel method, wherein the pluralities of POSS-cages undergo hydrolysis and polycondensation reactions at the alkoxide groups on the flexible arms, to form the Si—O—Si linkages of the covalently-linked network. With the proper choice of reagents, Ca$^{+2}$ ions are also incorporated in the resultant hybrid glass, giving it its bioactive property.

In terms of material requirements, bioactive glasses by sol-gel processing, which exhibit calcium phosphate nucleation and accurately mimic the in vivo bone mineral maturation, show appealing characteristics as scaffolds for bone tissue engineering, but are limited by their inherent brittleness. Nature can combine brittle minerals and organic molecules into hybrid composites that are highly organized to achieve exceptional fracture resistance.

The sol-gel method is based on the processes of controlled hydrolysis of compounds, usually alkoxides in an aqueous or organic solvent. The sol-gel method is beneficial due its ability to synthesize an inorganic network by a chemical reaction carried out at room temperature with cost effectiveness.

Alkoxides are ideal for sol-gel synthesis because they readily react with water during hydrolysis, and are readily soluable in a variety of organic solvents, such as alcohol. During hydrolysis, the alkane groups of the alkoxides are removed and replaced by an OH group to provide an Si—OH group.

After hydrolysis, the flexible arm R is characterized by the formula —X—Si[$R_4,R_5,R_6$], wherein $R_4$, $R_5$, and $R_6$ are the same or different, and at least one of said $R_4$, $R_5$, $R_6$ is a hydroxyl group, with the understanding that this at least one hydroxyl group comes from at least one alkoxide of the prior —X—Si[$R_1,R_2,R_3$]. It should be noted that, in some embodiments, not all alkoxy groups, $C_nH_{2n+1}$, of the flexible arm will be reacted to form —OH. In some embodiments, $R_4$ and $R_5$ is an —OH group, and in other embodiments, $R_4$, $R_5$ and $R_6$ are all —OH groups.

In some embodiments, the POSS-cage is reacted with soluble calcium alkoxide. Calcium alkoxide is beneficial due to its commercial availability at a low cost. During the sol-gel process, it is possible that $Ca^{+2}$ ions will be incorporated into the POSS-cage. The amount of water added in the hydrolysis step determines whether the alkoxides are completely hydrolyzed or not.

In some embodiments, where the POSS-cages include deprotonated oxygen atoms, $Ca^{+2}$ ions will be incorporated into the framework linked POSS-cage network. It will be appreciated that exchange of $Ca^{+2}$ in the POSS-cage with the acid in the solvent could result in the formation of Si—OH groups on the surface of the hybrid bioactive glass. The presence of $Ca^{+2}$ within the POSS-cages is significant to the bioactivity of the present invention and apatite formation. Upon information and belief, when the hybrid bioactive glass is incorporated in vivo, the exchange of the incorporated $Ca^{+2}$ ions within a POSS-cage with the $H^+$ ions in normal body fluid will result in the formation of Si—OH groups on the surface of the present invention, and the Si—OH group could be the nucleation center of the Hap crystal growth to promote Hap formation, as found in bone or dental enamel.

In some embodiments, the sol-gel method includes a solvent. In some embodiments, the solvent is an organic solvent. Common organic solvents act as a reactant, as well as a control agent for particle growth. In some embodiments, the solvent is alcohol. In some embodiments, the alcohol includes a hydroxyl (—OH) functional group in the alcohol molecule. In some embodiments, the solvent is ethanol.

Hydrolysis often requires an excess of water and/or the use of a hydrolysis catalyst. In some embodiments, an acid catalyst is used to facilitate the hydrolysis reaction. During hydrolysis, the acid will remove the ethyl groups contained on each flexible arm attached to the POSS-cage and further react with the hydroxyl group of the alcohol, thereby transforming R1, R2 and R3 to —OH groups.

In some embodiments, the acid catalyst is selected from (i) HCl, (ii) formic acid or (iii) HF.

In some embodiments, each POSS-cage will covalently link to another POSS-cage through an Si—O—Si linkage formed through the polycondensation reaction during the sol-gel method. It should be appreciated that the more flexible arms which extend from a POSS-cage, the number of Si—O—Si linkages formed will increase.

During the condensation, a small molecule, such as water or alcohol will be liberated. The functionality of each flexible arm located on the POSS-cage will lead to the formation of the network, because when fully hydrolyzed, the POSS-cage is multi-functional and can covalently link to multiple other POSS-cages.

In some embodiments, the flexible arm R on the POSS-cage is characterized by the formula —X—Si[$R_4,R_5,R_6$], wherein at least $R_4$ is an —OH group. In some embodiments, $R_4$ and $R_5$ is an —OH group, and in other embodiments, $R_4$, $R_5$ and $R_6$ are all —OH groups.

The covalent Si—O—Si linkages are formed by the reaction of at least one hydroxyl group located on the flexible arm of a POSS-cage, and the at least one hydroxyl group located on the flexible arm of another POSS-cage during polycondensation. The reaction between the hydroxyl groups will lead to a covalent Si—O—Si linkage between two POSS-cages and the release of water.

In light of the foregoing, it should be appreciated that the present invention significantly advances the art by providing a hybrid bioactive glass that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Materials

Octavinyloctasila-sesquioxane (PSS-Octavinyl substituted), triethoxysilane, Alizarin Red S, Platinum (0)-1,3-divinyl-1,1,3,3-tetramethyldisiloxane complex solution in xylene, and other chemicals were purchased from Sigmae-Aldrich (St. Louis, Mo.).

Synthesis of POSS-Derived Precursor 0.15 mL of Pt catalyst was added to a stirred mixture of octavinyloctasilasesquioxane (0.5 g, 789.84 μmol) and triethoxysilane (2.6 g, 15.8 mmol) over 10 min. The temperature of the reaction mixture was controlled not exceed 30° C. The solution was then heated to 90° C. for 6 h, cooled down and stirred at room temperature overnight. The excess triethoxysilane was removed in vacuo at 50° C. to afford light yellow oil (1.12 g, yield: 77%).

POSS-Derived Hybrid Glass (PHG) Preparation

The PHG was prepared following the sol-gel method by incorporation of calcium alkoxide during the polycondensation process of the precursors. In a typical synthesis, POSS-derived precursor and 1.9 g (2 mmol) of calcium methoxyethoxide were dissolved in 2.5 mL of anhydrous ethanol together with 0.05 ml of aqueous HCl (1M) under argon atmosphere. The solution was then separated in Teflon molds. After 5-day incubation at room temperature, the sol was aged at 70° C. for 3 weeks and dried for 5 days at 95° C. After this process, homogeneous hybrid glasses were obtained with different sizes.

Characterization of POSS-Derived Hybrid Glass

Thermogravimetric (TG) analyses were carried out with the Thermal Analysis Instrument (TGAQ500), under air atmosphere with a heating rate of 10° C./min.

Two-dimensional wide angle X-ray diffraction (2DWA-XRD) experiments were conducted on a Rigakua 18 kW rotating anode X-ray generator using Cu Kα radiation (0.1542 nm) in transmission mode.

Solid NMR spectra were performed on a Bruker Avance 300 with carrier frequencies of 300.3 and 59.6 MHz for $^1$H and $^{29}$Si, respectively. All experiments were performed using a 7-mm double-resonance probe. The chemical shift was externally referred to the silicon peak of TMS at 0 ppm. The RF field strength for both $^1$H and $^{29}$Si was fixed at 55.6 kHz, whereas the $^1$H—$^{29}$Si cross-polarization (CP) time and recycle delay (RD) time were 10 ms and 2 s, respectively. The MAS spinning frequency was set to 4 kHz.

Fourier transform infrared spectroscopy (FTIR) was carried out with Digilab Excalibur 3000 spectrometer. The spectra were scanned from 500 to 4000 cm$^{-1}$ using KBr technique and operating in the transmittance mode.

The mechanical properties of the two hybrid materials were tested at room temperature on an Instron Model 5567. The impermeable, unlubricated compression platens were lowered so as to contact the cylindrical sample (diameter=4.3-4.4 mm, thickness=1.0-1.1 mm, L/D<2) and produce a small, but detectable load (0.002 N). Samples were then compressed at a rate of 1 mm/min until a sharp decrease in stress was detected when the tests were stopped. Stress-strain curves were plotted. Young's modulus can be calculated by dividing the stress by strain, which is the slope of the initial linear portion of the stress-strain curve. Fracture toughness ($K_{Ic}$) also can be calculated according to Eq. (1).

$$K_{Ic} = \sqrt{EG} \tag{1}$$

Where, E is Young's modulus and G is critical strain energy release per unit area, which can be calculated from toughness according to Eq. (2), $$G = L \times \int_0^{\epsilon_f} \sigma d\epsilon \tag{2}$$

where L is the thickness of each cylinder sample, $\sigma$ is stress, and $\epsilon$ is strain, integrated from 0 to the critical break point ($\epsilon_f$). A minimum of three specimens was tested and data averaged.

Contact angle was used to quantitatively measure the surface hydrophobicity on Rame-Hart Instrument with contact angle goniometer. The pictures were taken at 3 different positions and processed by image J software to calculate the contact angle of each surface and the data were averaged.

In Vitro Bioactivity

Assessment of in vitro bioactivity was carried out by soaking the hybrid materials in 30 ml of filtered simulated body fluid (SBF) at 37° C. under sterile conditions. SBF was changed on day 1, 4, 7, 14, and 21. For each time point, we aspirated 3 mL of SBF out for analysis and replaced it with same volume of fresh solution. SBF has similar composition and ionic concentrations compared to human plasma. Concentrations of Ca and Si levels in solutions after soaking of the hybrid materials were determined by Inductively Coupled Plasma Optical Emission Spectroscopy (ICPOES). Solution pH was measured using the pH meter. Surface morphology of each hybrid material was observed by scanning electronic microscopy (SEM) in a JOEL 7401F microscope with detector for Energy-dispersive X-ray spectroscopy (EDX) analysis.

Cell Viability and Morphology

ADSCs (Lonza Walkersville Inc, Allendale, N.J.) at passage 5 were cultured in regular growth medium (αMEM supplemented with 10% fetal bovine serum, 100 u/mL penicillin/streptomycin), and incubated at 37° C. in a 5% $CO_2$ atmosphere. Cells were seeded onto hybrid materials (immobilized on the 24-well plates) at 5000 cells per cm$^2$, and incubated for 24 h.

The compatibility of hybrid materials was tested using Live/Dead viability/cytotoxicity assay kit (Invitrogen, CA). Following incubation, combined Live/Dead cell staining solution (2 μM calcein AM and 4 μM EthD-1 in PBS) was added on the hybrid material surface and incubated with cells for 5-10 min at room temperature. Images were obtained using IX51 Epifluorescence Microscope (Olympus Co., Japan) equipped with fluorescence light source and filters. The viability was calculated at 5 different positions of the hybrid material surface and processed by counting the number of viable cells and dead cells.

The cell adhesion patterns on the hybrid material surface were visualized by actin staining. ADSCs were seeded on the hybrid material surface and cultured at 37° C. for 24 h. Cells were washed with PBS twice and fixed in 3.6% paraformaldehyde in PBS (pH 7.4) for 10 min at room temperature. After fixation, cells were washed with PBS and then treated with 0.1% Triton X-100 in PBS for 5 min and blocking solution (1% BSA in PBS) for 20 min. After the blocking solution was aspirated out, the cells were washed with PBS twice and then treated with fluorescent tetramethylrhodamine phalloidin (TRITC-conjugated phalloidin, Invitrogen), co-stained with 4',6-diamidino-2-phenylindole (DAPI). Images were obtained under Epifluorescence Microscope.

Preliminary Osteogenic Differentiation Studies

Osteogenic differentiation was induced in osteogenic medium (growth medium with 0.1 μM dexamethasone, 10 μM β-glyeroal phosphate, 0.2 mM ascorbic acid-2-phosphate), which was changed twice a week. Alkaline phosphatase (ALP) staining was performed on day 14 following the standard protocol. Briefly, the medium was aspirated out from each well, and cells were washed with PBS twice and fixed with 10% buffered formalin for 15 min at room temperature. Then the cells were rinsed twice with PBS and Milli-Q water followed by addition of 1 ml of 1-Step™ NBT/BCIP (Thermo Scientific) solution for 20 min. Finally, the wells were washed with Milli-Q water, and stains were visualized under a microscope.

For ALP quantitation assay, cells on the PHG were lysed with 0.2% Triton-X100. Aliquots (20 μl) of the cell lysates were transferred into a 96-well plate. The concentration of ALP was analyzed by ANASpec SensoLyte™ FDP kit (Anaspec®) using standard procedures. Total DNA was also measured by CyQuANT Assay (Invitrogen, CA). Cell differentiation was expressed as ALP amount normalized to total DNA. A minimum of four specimens was tested and the data were averaged.

Cells were extended to incubate on the surface of PHG for 21 days in osteogenic medium. Alizarin Red S staining was performed following the standard protocol. Briefly, the culture medium was removed from each well, and the cells on PHG were washed 3 times with PBS. The cells were fixed with 10% buffered formalin for 15 min at room temperature, and then rinsed twice with PBS and Milli-Q water followed by addition of 1 ml of Alizarin Red S (ARS, Sigma-Aldrich, 40 mM) solution for 30 min. Finally, the wells were washed with Milli-Q water five times, and calcium deposition was stained orange-red.

Statistical Analysis

Means and standard deviation (SD) were obtained. Student's T-test was conducted to analyze differences and a p-value less than 0.05 was considered statistically significant.

Results and Discussion

Hybrid bioactive glasses were prepared by hydrolysis and condensation with calcium alkoxide of a precursor in accordance with FIG. 1, with flexible arms of —$CH_2CH_2$—Si—($OCH_2CH_3$)$_3$. Energetically, it is unfavorable for one POSS cage to form two bonds with another POSS cage. Thus, for each POSS cage, it could potentially crosslink with up to eight other POSS cages (shown schematically in Scheme 1b). The organic phase is formed by this sol-gel process, and the inorganic structures are distributed homogeneously within the organic phase on a molecular scale to form the bulk material. This process allows tailoring the shape and size of the hybrid bioactive glass by using molds with different shapes and/or changing the amount of precursor (Scheme 1c). As control, precursor A (Si[CH2CH2Si (OC2H5)3]4) was also synthesized and the corresponding star gel A (SGA) was prepared following the same process as with PHG. These two hybrid materials possess the same $Ca^{+2}$/precursor ratio of 1/1.

PHG Characterization

Figure 3:
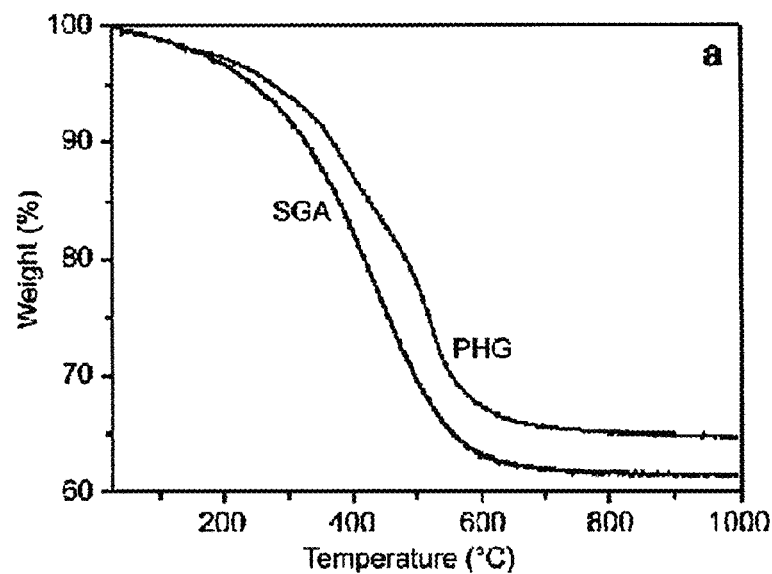
FIG. 3 is a graph representing weigh loss of the invention due to the decomposition of the organic component compared to star-gel material (SGA)
Figure 4:
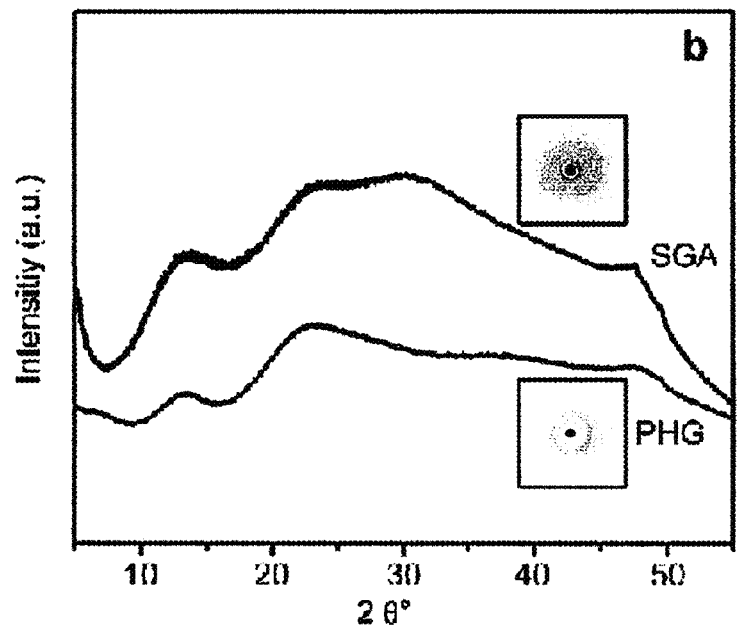
FIG. 4 is a graph representing the diffraction peaks of the amorphous materials of the present invention compared to SGA.
Figure 5:
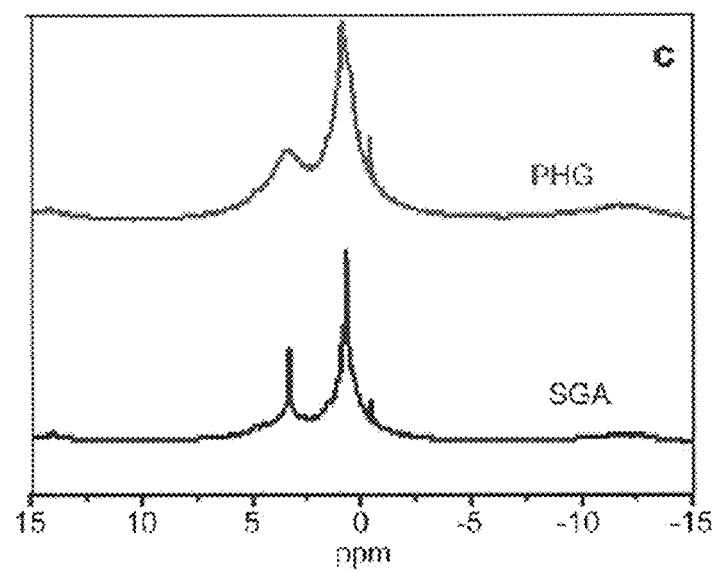
FIG. 5 is a graph representing the "wide-line" spectrum of the hybrid bioactive glass compared to SGA.
Figure 6:
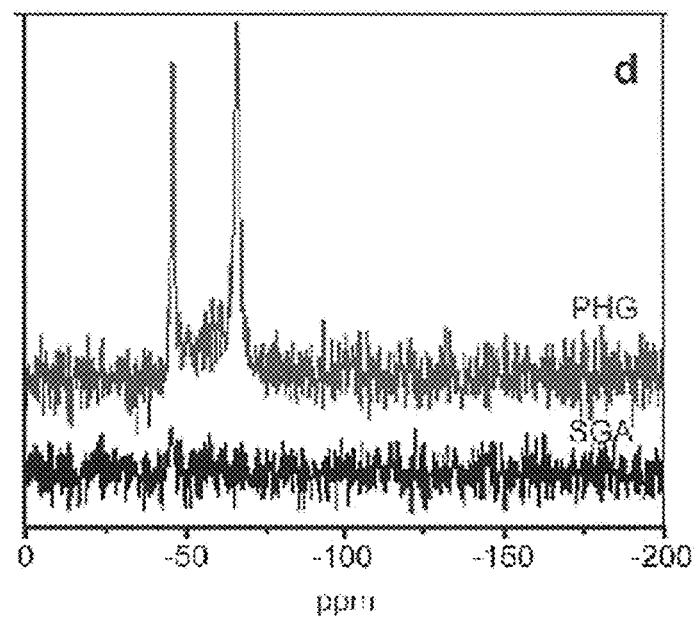
FIG. 6 is a graph representing spectrum of the hybrid bioactive glass compared to SGA.

TG patterns of both Ca-containing hybrid materials exhibited around 35%-40% weight losses (FIG. 3), corresponding to the decomposition of the organic component. Broad diffraction peaks of amorphous materials are shown by XRD for both hybrid materials (FIG. 4), which demonstrate the crystalline phase aggregation does not occur during this sol-gel process. $^1H$ solid state NMR (FIG. 5) shows the "wide-line" spectrum of PHG compared to SGA. $^{29}Si$ solid state NMR (FIG. 6) of SGA shows very weak $^{29}Si$ signal at ~-46 ppm, while PHG displays two sharp signals at -46 ppm and -66 ppm. All these results indicate that the cross-polarization (CP) efficiency between $^1H$ and $^{29}Si$ in PHG is stronger than in SGA, suggesting the lower and slower mobility of $^1H$ and $^{29}Si$ in the network of PHG than in SGA.

Mechanical Properties

Figure 7:
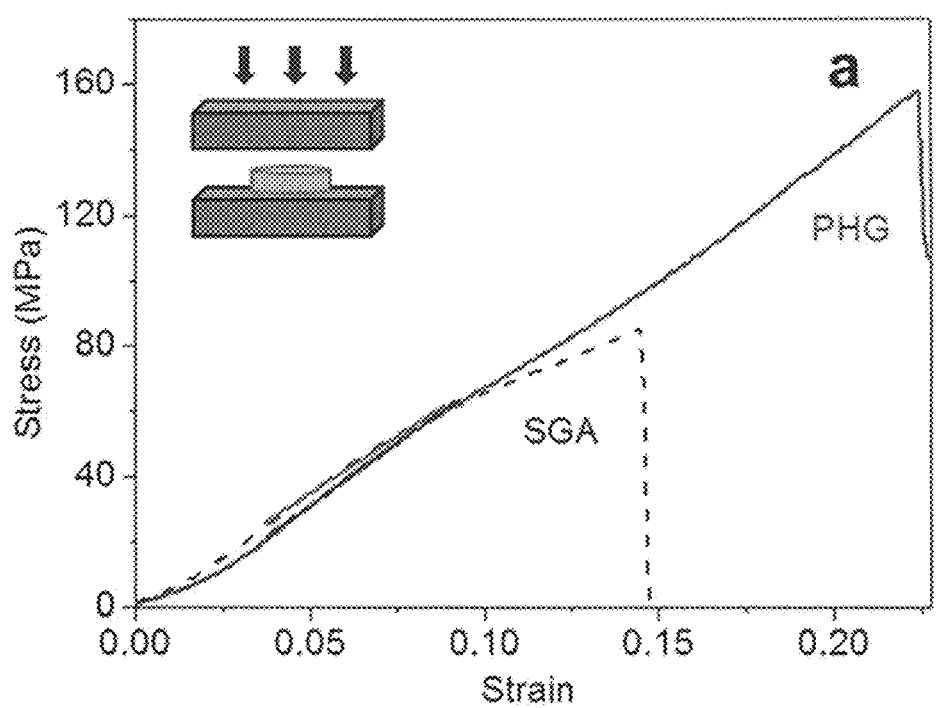
FIG. 7 is a graph representing the mechanical properties of the hybrid bioactive glass compared to SGA.
Figure 10:
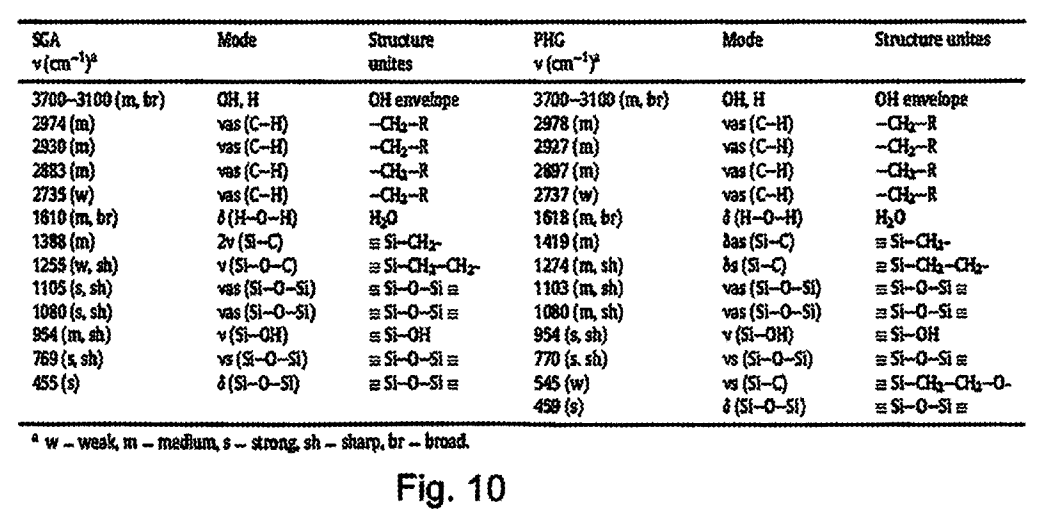

Structured materials are usually associated with unique mechanical and biological properties. Although the two materials showed similar FTIR absorption bands corresponding to the same functional groups (FIG. 10), and both inorganic and organic phase in each hybrid material are well-integrated at molecular level, the mechanical properties are significantly different (FIG. 7). The Young's modulus, a measure of the stiffness of an elastic isotropic material, mainly depends on elastic forces of the chemical bonds. In both hybrid networks, C—C bond should be the site of failure because of a lower bond energy (346 kJ/mol) when compared to the Si—O (452 kJ/mol) and Si—C (381 kJ/mol) bonds. The organic component in SGA makes geometrical configuration flexible, which results in lower average modulus (692.1±16.8 MPa). In the case of PHG, the higher modulus (769.5±13.4 MPa) can be achieved (p<0.05) due to the higher Si—O inorganic composition and the higher Peierls-Nabarro forces that limit dislocation mobility (FIGS. 5 &6) associated within the rigid POSS structure. This invariability usually results in more brittle behavior and poor toughness. However, the corresponding fracture toughness of PHG (3.56±0.25 $MPa·m^{1/2}$) is almost double of that of SGA (1.95±0.17 $MPa·m^{1/2}$, p<0.05). To help further understand the structural difference between SGA and PHG, molecular schematics of the two materials were built with Chem3D 10.0 and the structures were optimized by energy minimization using MM2 method. The flexible structure of SGA allows rotation and deformations resulting in material with better toughness than conventional Bioglass®(0.5-1 $MPa·m^{1/2}$). In PHG, the structure replicates the nanoscale phenomena at the microscopic dimensions observed in natural materials. Eight organic bonds on each silsesquioxane unit can act as elastic springs as well as the sacrificial bonds, which make the POSS cage undergo "elastic deformation" at limited scale along the stress direction to dissipate energy. Furthermore, within the PHG network, there are some unoccupied spaces (free volumes) between molecules due to the steric effects associated with POSS structure. These free volumes also can contribute high intermolecular force and contribute high fracture toughness. The structure effects of PHG produce a strong influence on the fracture toughness, similar to human tibia (2.4-5.3 $MPa·m^{1/2}$) in longitudinal direction.

In Vitro Bioactivity

Figure 8:
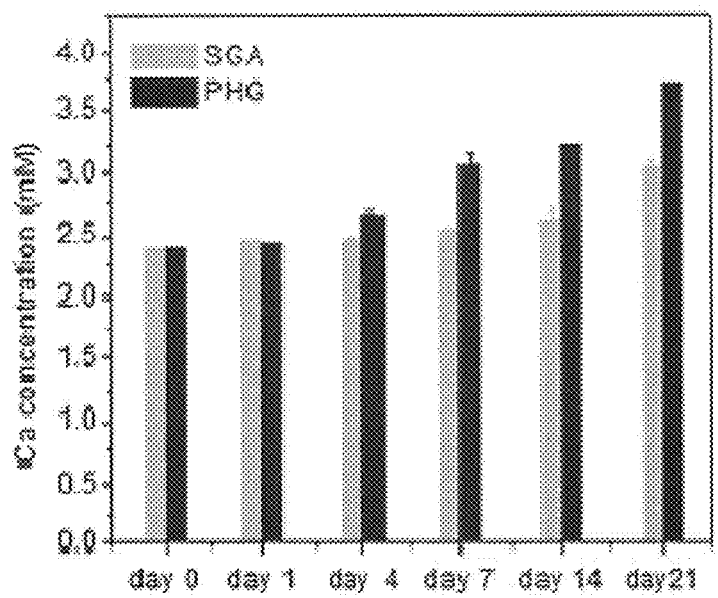
FIG. 8 is a graph representing the release of $Ca^{+2}$ ions for apatite formation on the hybrid bioactive glass surface.
Figure 9:
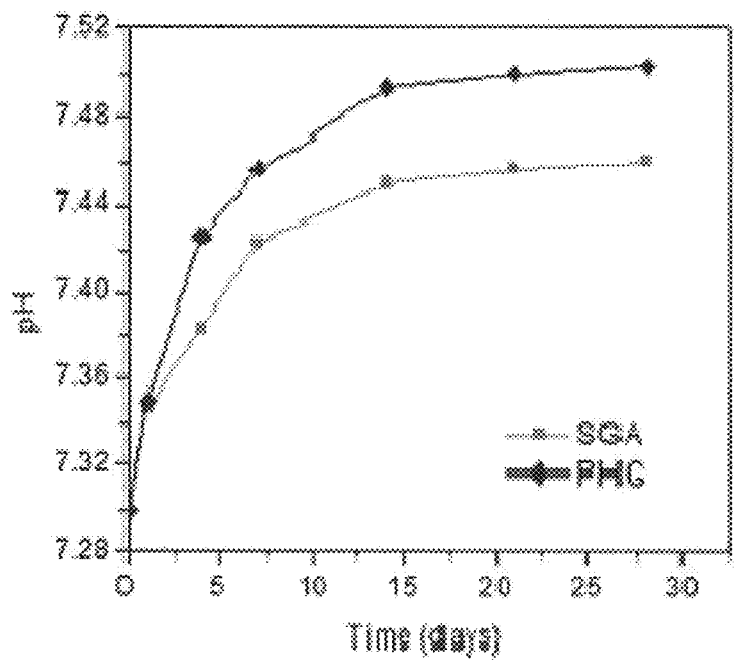
FIG. 9 is a graph representing the increase of pH used for apatite formation on the hybrid bioactive glass surface.

In previous studies, dispersion of micro or nanoscale inorganic bioglasses (BGs) in polymers have been shown to improve crack resistance of scaffolds. However, by incorporating the bioactive inorganic particles into a polymer matrix, the bioactivity was attenuated because most of the BGs were covered. Conventional bioactivity tests, where the scaffolds were immersed in simulated body fluid (SBF), showed that HAP formation only occurred on the surface of BGs. A confluent HAP layer was formed over 21 days as the polymer phase degraded and the BGs exposed. This indicated that bonding to the bone would be slow in vivo. In the present work, immersion in SBF was also used to evaluate the in vitro bioactivity of the two hybrid materials. Although silicate release was not observed in the first 21 days (data not shown), the $Ca^{2+}$ release (FIG. 8) and the increase of pH (FIG. 9) in SBF for both hybrid materials are in agreement with the mechanism proposed by Kokubo for apatite formation on the BG surface. During this period, the exchange of $Ca^{2+}$ in the hybrid with $H^+$ in solution could result in the formation of Si—OH groups on the surface, and induce apatite nucleation. Surface characterization of the SEM images and the corresponding EDX spectrum of SGA after immersion in SBF for 7 and 14 days. On day 7, the micrograph for SGA did not show any visible mineralization. By day 14, apatite crystals had formed on the surface of SGA with a needle-like morphology and aggregated to form random spherical-shaped clusters; the morphology which is typical of the many reports in the literature. While, apatite crystals synthesized on the surface of PHG exhibited a plate-like morphology and constructed a 3D flower-like structure on day 7, indicating the mineralization cascade may be accelerated. This result is rather interesting because HAP crystals in vertebrate long bones and tooth enamel have a plate-like morphology.

Cell Viability and Morphology

For preliminary biocompatibility studies and tests of in vitro cell adhesion and differentiation, human adipose tissue-derived stem cells (ADSCs) were cultivated on both sterilized hybrid materials. ADSCs share many characteristics with their bone marrow counterparts, including extensive proliferative potential, lack of immunogenicity, and the ability to differentiate toward adipogenic, osteogenic, chondrogenic, and myogenic lineages. The viability of ADSCs after incubation on the surface of each hybrid material for 24 h was evaluated using Live/Dead staining with calcein-AM and ethidium homodimer in standard growth medium. Fluorescence microscopy revealed that most of the cells plated on PHG were alive (99.2±0.8%, n=5, p<0.05) and maintained their spindle-like shape. However, in the case of SGA, almost no cell adhesion was observed on the surface. This finding was attributed to the hydrophobic character of the surface, which was supported by the higher (p<0.05) water contact angle (136.0±1.6°) for SGA compared to the water contact angle (96±1.8°) of PHG. To examine cell spreading patterns oh PHG, ADS Cs were stained with TRITC-conjugated phalloidin to reveal the actin filament network. These stem cells presented the usual elongated structure with noticeable filopodia extensions and cellular propagation fronts. This morphological analysis suggests that PHG is biocompatible to cells respect to adhesion and spreading.

ADSCs Differentiation into Osteogenic Lineages

ADSCs at passage 5 cultured on the surface of PHG in osteogenic medium subsequently showed osteogenic differentiation behavior. Alkaline phosphatase (ALP) is a membrane-bound glycoprotein and is highly expressed in osteoblasts. It has been used as a standard early osteogenic differentiation marker to determine the conversion of ADSCs into osteoblasts in osteogenic medium. On day 14, quantitative ALP-specific enzymatic analysis and ALP staining indicated the expression level of ALP in cells on PHG surface (0.0232±0.0019 µg ALP/µg DNA, n=4), which was significantly higher than those on the commercial polystyrene surface (0.0142±0.0021 µg ALP/µg DNA, n=4, p<0.05). Interestingly, our results showed that PHG can stimulate ADSCs to differentiate into the osteogenic lineage cells in growth medium even in the absence of osteogenic agents such as dexamethasone, β-glycero-2-phosphate, and ascorbic acid-2-phosphate. ADSCs cultured on the PHG exhibited ALP expression after 14 days of incubation in standard cell growth medium. After extending the culture time to 21 days in osteogenic medium, it was found that ADSCs had developed a mature in vitro osteoblast phenotype that results in the formation of mineralization nodules and calcified layer on PHG, detected by Alizarin Red staining. The corresponding EDX spectrum of the layer is shown. This is a significant marker of potential bone formation. We considered the PHG can anchors the cells firmly to provide them enough space to spread. The release of $Ca^{2+}$ activates a cascade of intracellular signaling pathways and thus guides the cells to differentiate and fulfill their function efficiently. Therefore, PHG could be used as a high-performance biomaterial for application in bone tissue engineering.

CONCLUSION

By appreciating the unique fracture resistance structures of natural materials (such as bone and nacre) and mimicking their toughening mechanisms on the nanometer scale, we have synthesized a new POSS-derived hybrid glass with specific toughness properties that can match those of the natural bone. This hybrid glassy material exhibits excellent bioactivity to form plate-like apatite on the surface after soaking in SBF. This bioactive hybrid glass also offers a platform on which ADSCs can adhere and differentiate to osteoblasts. These results highlight the tremendous potential of the biomimetic approach and suggest promising strategies for structural optimization. The key structural features of this material can be used to guide the design of bio-inspired composites with unique toughness, which would be of great benefit to hard tissue engineering.

What is claimed is:

1. A hybrid bioactive glass to be utilized for biotissues, tissue engineering or bone scaffolds, the hybrid bioactive glass comprising:
a plurality of POSS-cages each having at least one flexible arm radiating from an Si atom of the POSS-cage, each POSS-cage being covalently linked to another POSS-cage through an —(Rx,OH)Si—O—Si(Ry,OH)— linkage between two of said flexible arms to form a covalently-linked network, wherein Rx and Ry are independently selected from the group consisting of organic groups, alkoxy groups and hydroxyl groups.

2. The hybrid bioactive glass as in claim 1, wherein each said POSS-cage is covalently bonded to at least 2 other POSS-cages.

3. The hybrid bioactive glass as in claim 2, wherein said flexible arms include an arm extension between the —(Rx, OH)Si—O—Si(Ry,OH)— linkage and the Si atom of the POSS cage, the arm extension being an alkane chain of 10 carbon atoms or less.

4. The hybrid bioactive glass as in claim 2, wherein said flexible arms include an arm extension between the —(Rx, OH)Si—O—Si(Ry,OH)— linkage and the Si atom of the POSS cage, the arm extension being an alkane chain of at least 2 carbon atoms.

5. The hybrid bioactive glass as in claim 2, wherein said POSS-cage comprises a cage structure selected from one of (i) 6 Si atoms, (ii) 8 Si atoms, (iii) 10 Si atoms, or (iv) 12 Si atoms.

6. The hybrid bioactive glass as in claim 5, wherein said POSS-cage comprises a cage structure of 8 Si atoms.

7. The hybrid bioactive glass as in claim 1, wherein said each POSS-cage is crosslinked to another POSS-cage to form said covalently-linked network.

8. The hybrid bioactive glass as in claim 1, where Rx and Ry are hydroxyl groups.

9. A method of forming a hybrid bioactive glass comprising the steps of:
(a) providing a plurality of POSS-cages, each having at least one reactive flexible arm radiating from an Si atom, wherein said reactive flexible arm is represented by the formula —X—Si[R1,R2,R3], wherein X is an arm extension, wherein R1, R2 and R3 are also the same or different, and at least one of said R1, R2 and R3 is an alkoxide; and
(b) reacting said plurality of POSS-cages through a sol-gel method employing a calcium alkoxide to form a covalently-linked network and incorporating $Ca^{+2}$ ions into the covalently-linked network so formed, said sol-gel process comprising hydrolysis and polycondensation reactions forming Si—O—Si linkages, wherein X is located between the Si—O—Si linkages and an Si atom of the POSS-cage, and wherein during hydrolysis at least one of said R1, R2 and R3 is converted to an hydroxyl group.

10. The method of forming a hybrid bioactive glass as in claim 9, wherein at least one of said R1, R2 and R3 is selected from —OCnH2n+1.

11. The method of forming a hybrid bioactive glass as in claim 10, wherein n is less than 10.

12. The method of forming a hybrid bioactive glass as in claim 9, wherein R1 is an ethoxy group.

13. The method of forming a hybrid bioactive glass as in claim 9, wherein R1 is a methoxy group.

14. The method of forming a hybrid bioactive glass as in claim 9, wherein R1 is a prop oxy group.

15. The method of forming a hybrid bioglass as in claim 9, wherein said hydrolysis reaction of said step of reacting employs a solvent and an acid catalyst.

16. The method of forming a hybrid bioglass as in claim 15, wherein said solvent is ethanol.

17. The method of forming a hybrid bioglass as in claim 15, wherein said acid catalyst is HCl.

18. The method of forming a hybrid bioglass as in claim 15, wherein said sol-gel method incorporates calcium alkoxide during the polycondensation reaction.

19. A hybrid bioactive glass manufactured by the process of claim 9.

* * * * *